United States Patent
Nett (10) Patent No.: US 10,561,391 B2
(45) Date of Patent: Feb. 18, 2020

(54) METHODS AND SYSTEMS FOR COMPUTED TOMOGRAPHY

(71) Applicant: General Electric Company, Schenectady, NY (US)

(72) Inventor: Brian Edward Nett, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 345 days.

(21) Appl. No.: 15/240,077

(22) Filed: Aug. 18, 2016

(65) Prior Publication Data

US 2018/0049714 A1 Feb. 22, 2018

(51) Int. Cl.
| | | |
|---|---|---|
| A61B 6/00 | (2006.01) | |
| A61B 6/04 | (2006.01) | |
| A61B 6/02 | (2006.01) | |
| A61B 6/03 | (2006.01) | |

(52) U.S. Cl.
CPC .............. *A61B 6/542* (2013.01); *A61B 6/027* (2013.01); *A61B 6/032* (2013.01); *A61B 6/0407* (2013.01); *A61B 6/0457* (2013.01); *A61B 6/461* (2013.01); *A61B 6/488* (2013.01); *A61B 6/544* (2013.01)

(58) Field of Classification Search
None
See application file for complete search history.

(56) References Cited

U.S. PATENT DOCUMENTS

| | | | |
|---|---|---|---|
| 5,379,333 A | 1/1995 | Toth | |
| 6,185,271 B1 * | 2/2001 | Kinsinger | A61B 6/032 378/19 |
| 7,695,193 B2 | 4/2010 | Flohr et al. | |
| 2006/0262896 A1 | 11/2006 | Nishide et al. | |
| 2007/0286332 A1 * | 12/2007 | Gohno | A61B 6/032 378/15 |
| 2009/0092224 A1 * | 4/2009 | Nishide | A61B 6/032 378/13 |
| 2015/0351709 A1 * | 12/2015 | Dirauf | A61B 6/545 378/206 |

FOREIGN PATENT DOCUMENTS

JP   2007275551 A   10/2007

OTHER PUBLICATIONS

Gies, M. et al., "Dose reduction in CT by anatomically adapted tube current modulation. I. Simulation studies," Medical Physics, vol. 26, No. 11, Nov. 1999, 13 pages.

(Continued)

*Primary Examiner* — Hoon K Song
(74) *Attorney, Agent, or Firm* — McCoy Russell LLP (57) ABSTRACT

Methods and systems are provided for automatic exposure control in a computed tomography imaging system. In one embodiment, a method comprises estimating attenuation properties of a subject along a direction, and varying, based on the attenuation properties, a helical pitch along the direction during a scan of the subject. In this way, a desired image quality can be maintained while reducing radiation dose, without modulating tube current.

20 Claims, 7 Drawing Sheets

(56) References Cited

OTHER PUBLICATIONS

Goetti, R. et al., "Quantitative Computed Tomography Liver Perfusion Imaging Using Dynamic Spiral Scanning With Variable Pitch: Feasibility and Initial Results in Patients With Cancer Metastases," Investigative Radiology, vol. 45, No. 1, Jul. 2010, 8 pages.

Singh, J. et al., "Role of Perfusion CT Differentiating Hemangiomas from Malignant Hepatic Lesions," Journal of Clinical Imaging Science, vol. 4, No. 10, Feb. 27, 2014, 9 pages.

"Low Dose (Low Dose Solution of CT [Workflow])," Toshiba Medical Website, Available Online at http://www.toshibamedicalsystems.com/products/dose/lowdose/workflow.html, Available as Early as May 10, 2016, As Retrieved Aug. 18, 2016, 4 pages.

Invitation to Pay Additional Fees for corresponding PCT application PCT/US2017/045723 dated Nov. 20, 2017.

\* cited by examiner

METHODS AND SYSTEMS FOR COMPUTED TOMOGRAPHY

FIELD

Embodiments of the subject matter disclosed herein relate to non-invasive diagnostic imaging, and more particularly, to automatic exposure control in computed tomography imaging systems.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures).

Modern CT systems include automatic exposure control (AEC) configured to set the dose operating point to achieve optimized performance between image quality and radiation dose. Typically, automatic exposure control involves modulating a tube current applied to an x-ray source during a scan, so that the lowest necessary radiation dose is delivered while maintaining a desired image quality.

However, some CT imaging modes preclude tube current modulation. For example, for dual energy imaging, the x-ray source rapidly switches between different peak tube kilovoltages (kVp) in order to resolve different materials within the subject being scanned. Due to the rapid kVp switching, the generator may not allow modulation of the tube current. Furthermore, for some imaging scenarios, physical constraints of tube current modulation may render such an approach insufficient for automatic exposure control.

BRIEF DESCRIPTION

In one embodiment, a method comprises estimating attenuation properties of a subject along a direction, and varying, based on the attenuation properties, a helical pitch along the direction during a scan of the subject. In this way, a desired image quality can be maintained while reducing radiation dose, without modulating tube current. It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 3:
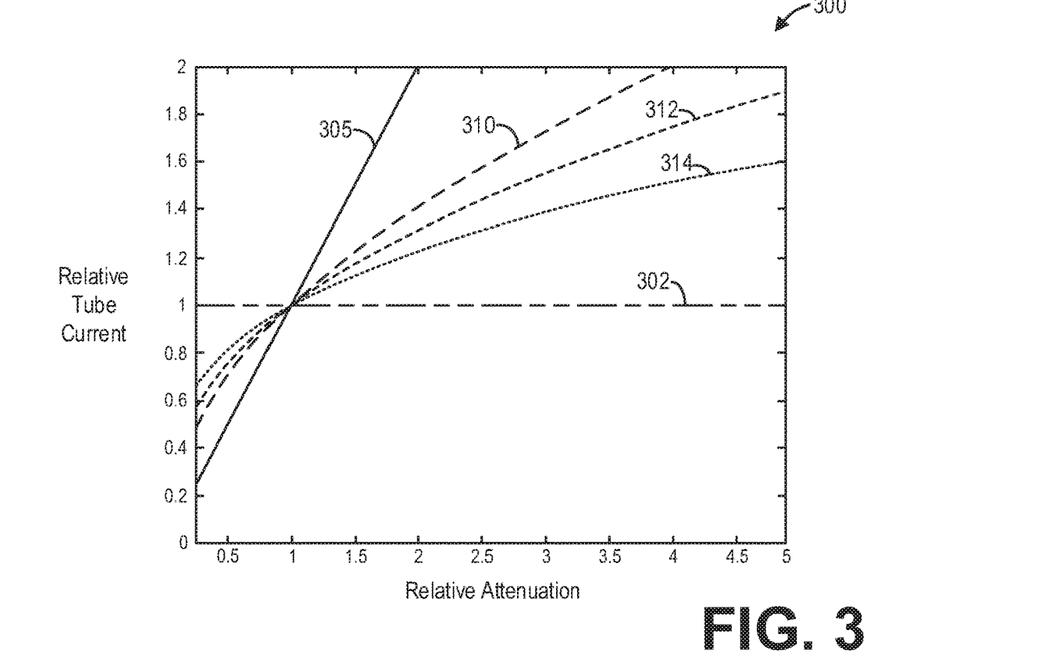
FIG. 3 shows a graph illustrating example attenuation-based tube current modulations for controlling image noise.
Figure 4:
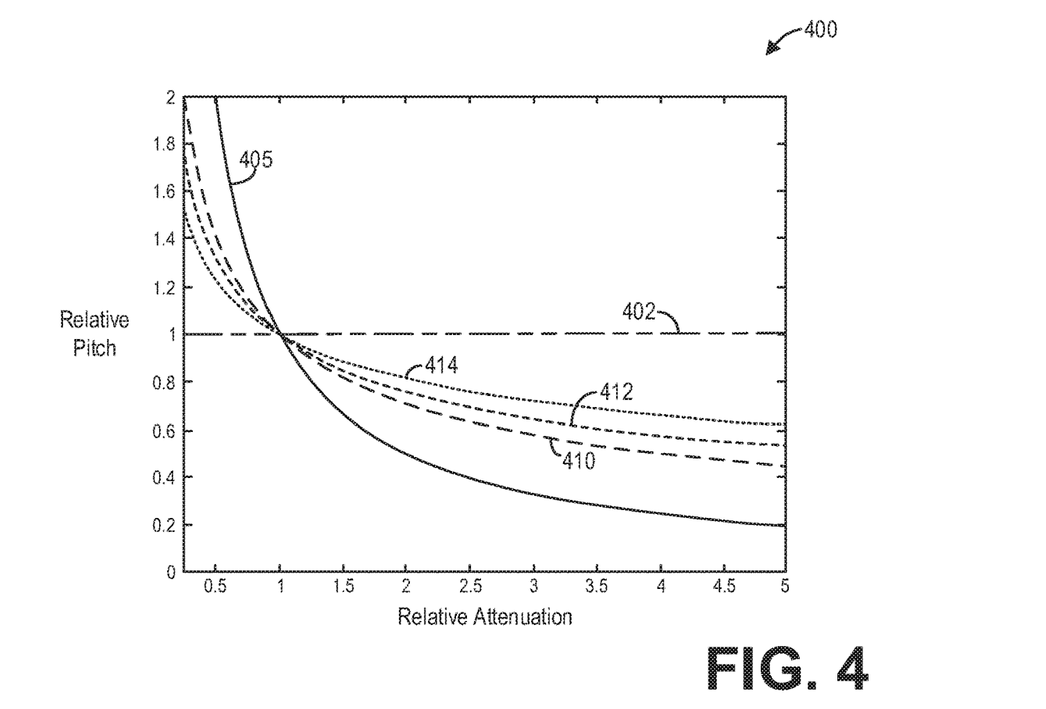
FIG. 4 shows a graph illustrating example attenuation-based pitch modulations for controlling image noise according to an embodiment of the invention.
Figure 6:
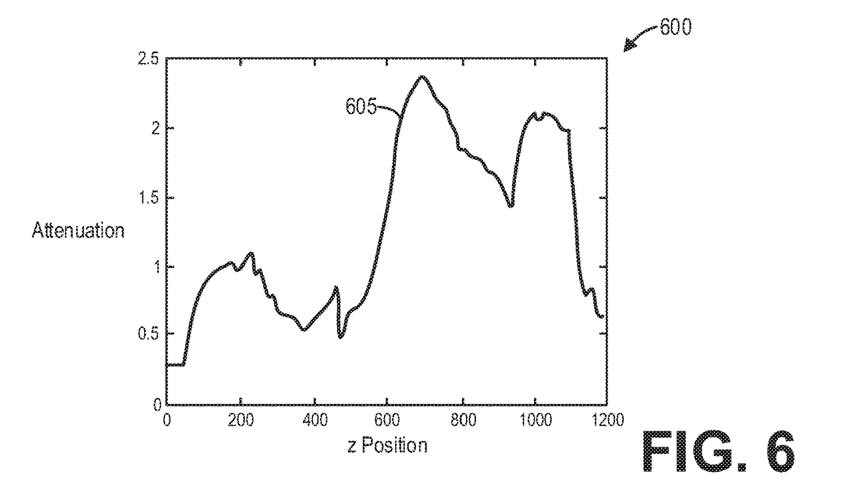
FIG. 6 shows a graph illustrating an example attenuation map according to an embodiment of the invention.
Figure 7:
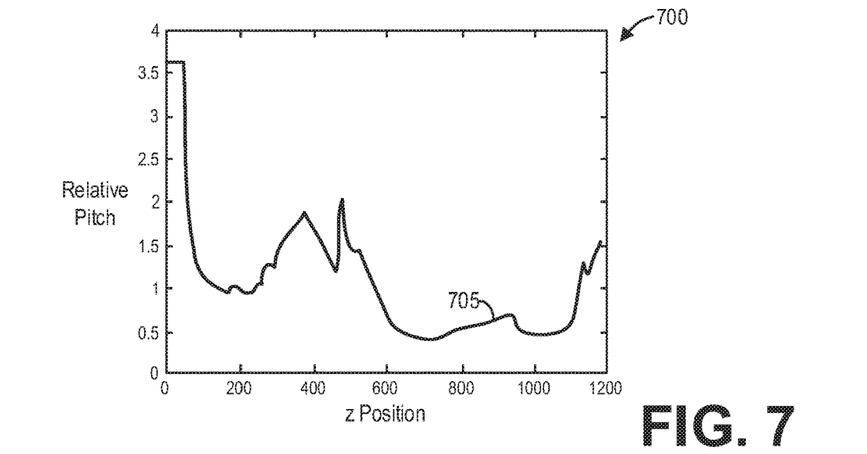
FIG. 7 shows a graph illustrating an example pitch profile according to an embodiment of the invention.
Figure 8:
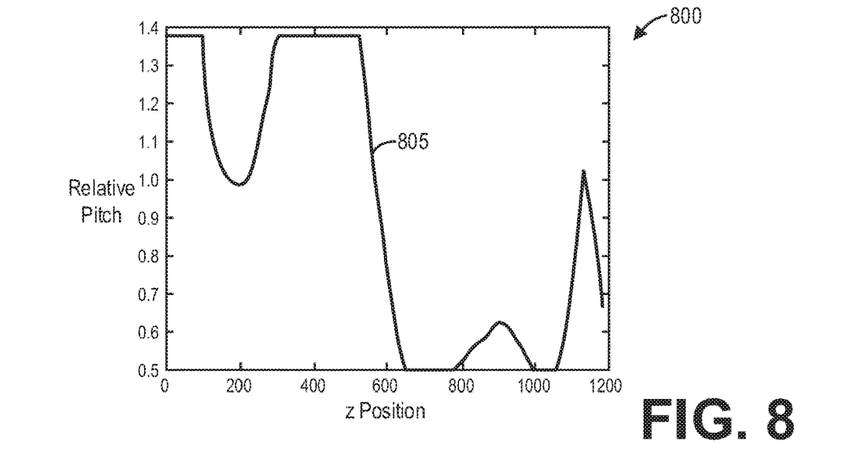
FIG. 8 shows a graph illustrating an example constrained pitch profile according to an embodiment of the invention.
Figure 9:
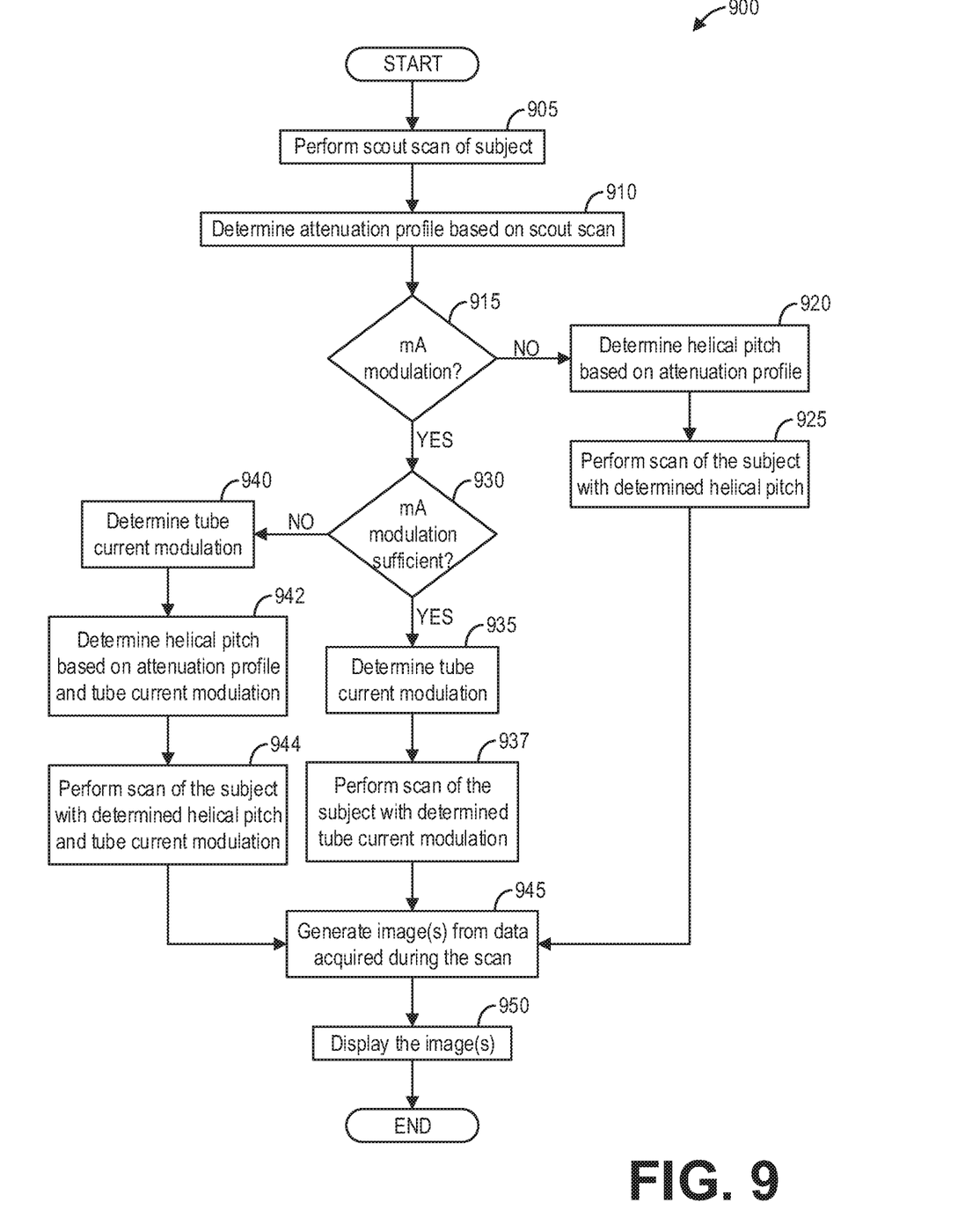
FIG. 9 shows a high-level flow chart illustrating an example method for automatic exposure control according to an embodiment of the invention.
Figure 10:
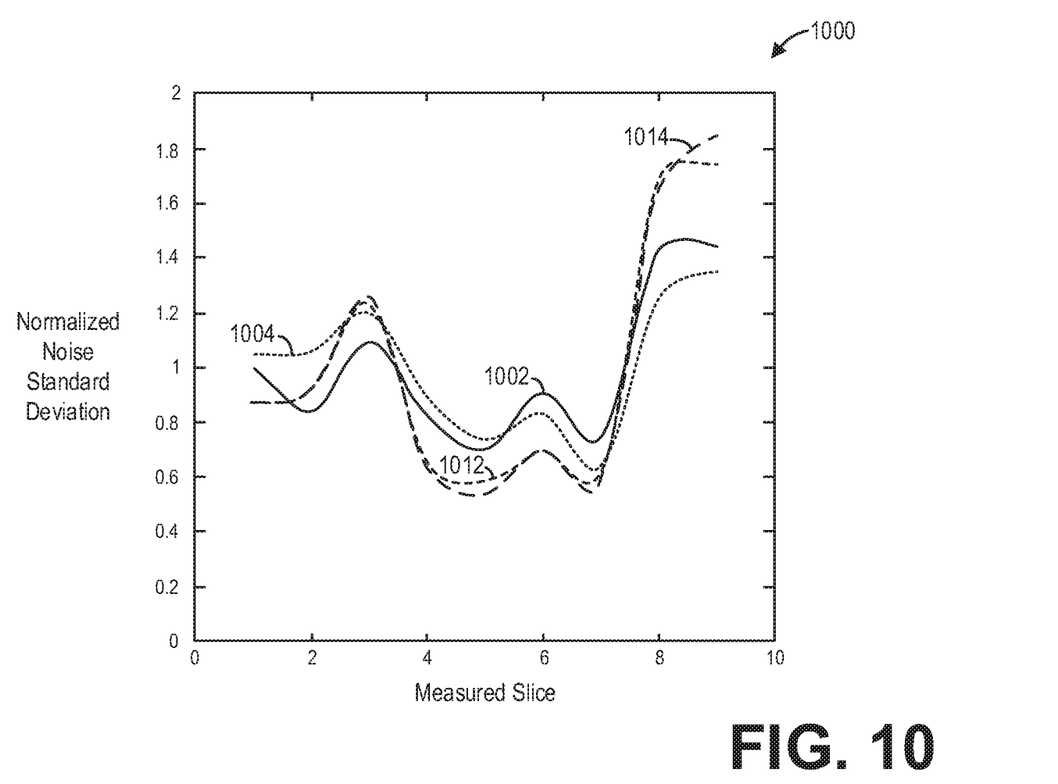
FIG. 10 shows a graph illustrating example image noise for different approaches to automatic exposure control.
Figure 11:
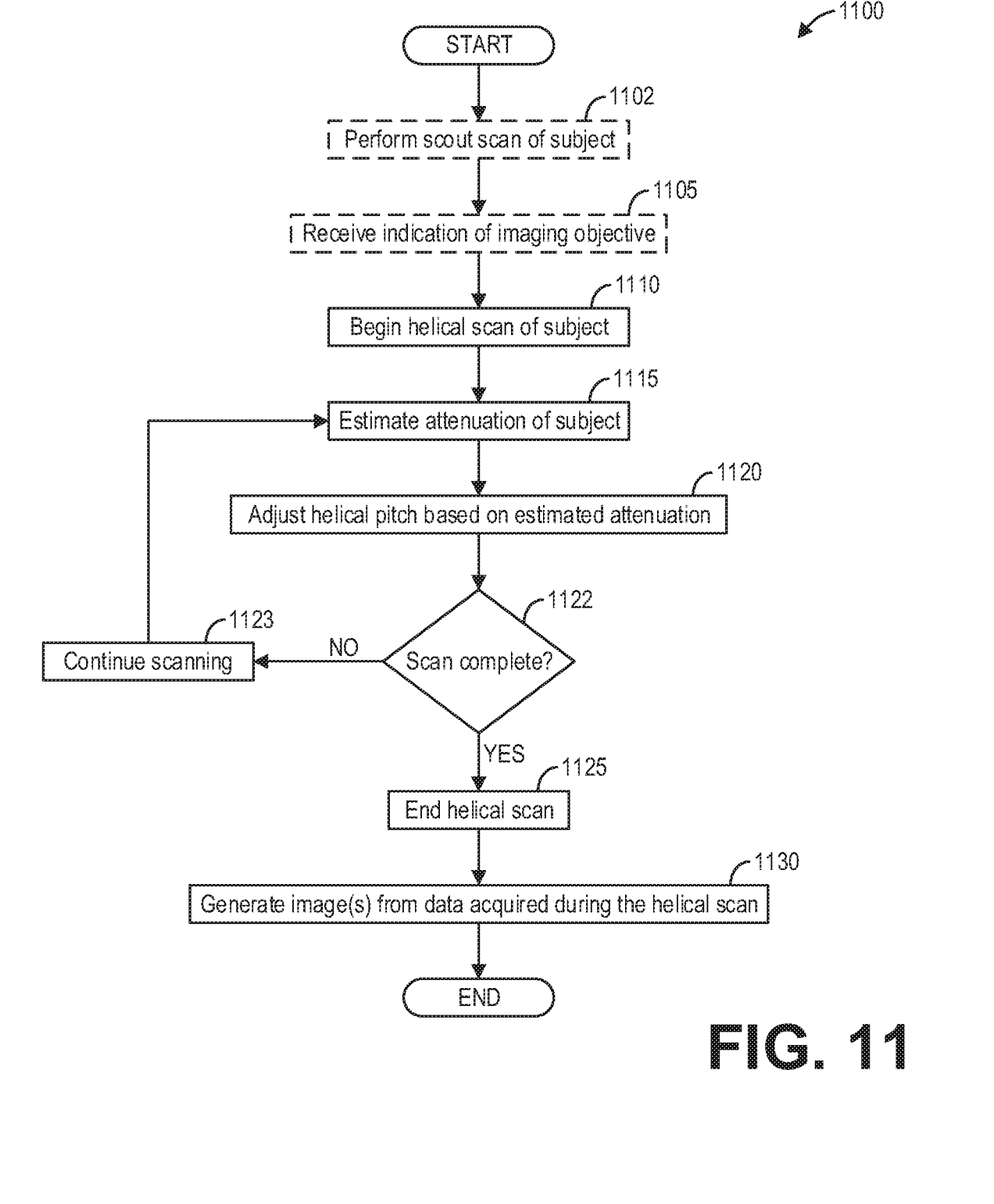
FIG. 11 shows a high-level flow chart illustrating an example method for automatic exposure control with dynamic helical pitch according to an embodiment of the invention.

The following description relates to various embodiments of medical imaging system. In particular, methods and systems are provided for variable pitch for automatic exposure control in CT imaging systems, such as the CT imaging system depicted in FIGS. 1 and 2. Typically, the current applied to an x-ray tube, or the tube current, is modulated during a scan to optimize the dose. FIG. 3 shows different relations between relative tube current and relative attenuation for different imaging objectives, such as constant image noise across the reconstruction volume. A different approach for automatic exposure control is the modulation of helical pitch, wherein the helical pitch is modulated during a scan to optimize the dose. FIG. 4 shows different relations between relative pitch and relative attenuation for different imaging objectives. A method for automatic exposure control, such as the method depicted in FIG. 5, includes determining an attenuation profile of the subject to be scanned, and then scanning the subject with a variable helical pitch based on the pre-determined attenuation profile. An example attenuation profile is shown in FIG. 6, and helical pitch modulations derived therefrom are shown in FIGS. 7 and 8. In some examples, automatic exposure control may be accomplished by using helical pitch modulation, tube current modulation, or a combination thereof, as shown in FIG. 9. The image noise performance of helical pitch modulation is comparable to tube current modulation, which are both superior to fixed pitch and tube current acquisitions, as shown in FIG. 10. In some examples, the helical pitch may be modulated based on attenuation estimates determined in real-time during a scan, without prior attenuation profile information, as depicted in FIG. 11.

Though a CT system is described by way of example, it should be understood that the present techniques may also be useful when applied to images acquired using other imaging modalities, such as tomosynthesis, C-arm angiography, and so forth. The present discussion of a CT imaging modality is provided merely as an example of one suitable imaging modality.

As used herein, the term "pixel" also includes embodiments of the invention where the data is represented by a "voxel." Thus, both the terms "pixel" and "voxel" may be used interchangeably herein.

As used herein, the phrase "reconstructing an image" is not intended to exclude embodiments of the present invention in which data representing an image is generated, but a viewable image is not. Therefore, as used herein, the term "image" broadly refers to both viewable images and data representing a viewable image. However, many embodiments generate (or are configured to generate) at least one viewable image.

Various embodiments may be implemented in connection with different types of imaging systems. For example, various embodiments may be implemented in connection with a CT imaging system in which an x-ray source projects a fan- or cone-shaped beam that is collimated to lie within an x-y plane of a Cartesian coordinate system and generally referred to as an "imaging plane." The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurement from all the detectors is acquired separately to produce a transmission profile.

In third-generation CT systems, the x-ray source and the detector array are rotated with a gantry within the imaging plane and around the object to be imaged such that the angle at which the x-ray beam intersects the object constantly changes. A complete gantry rotation occurs when the gantry concludes one full 360 degree revolution. A group of x-ray attenuation measurements (e.g., projection data) from the detector array at one gantry angle is referred to as a "view." A view is, therefore, each incremental position of the gantry. A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as a filtered backprojection (FBP) technique. This process converts the attenuation measurements from a scan into integers called "CT numbers" or "Hounsfield units" (HU), which are used to control the brightness of a corresponding pixel on, for example, a cathode ray tube display.

To reduce the total scan time for long superior-inferior extent, a "helical" scan may be performed. To perform a helical scan, the patient is moved in the z direction synchronously with the rotation of the gantry, while the data for the prescribed number of slices is acquired. Such a system generates a single helix from a fan- or cone-beam helical scan. The helix mapped out by the fan- or cone beam yields projection data from which images in each prescribed slice may be reconstructed. In addition to reducing scan time, helical scanning provides other advantages such as better use of injected contrast, improved image reconstruction at arbitrary locations, and better three-dimensional images.

Figure 1:
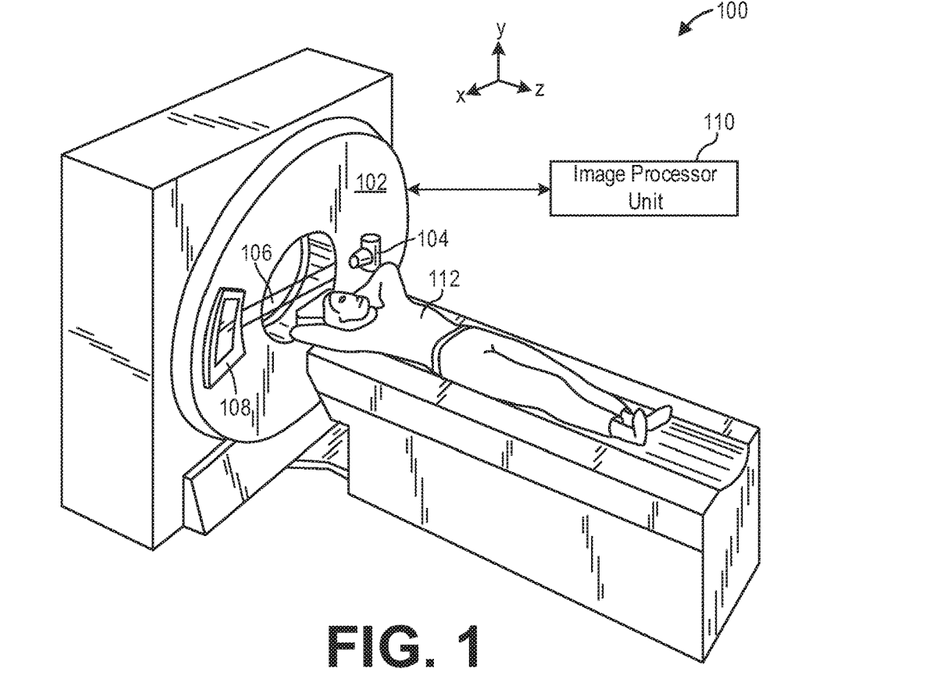
FIG. 1 shows a pictorial view of an imaging system according to an embodiment of the invention.

FIG. 1 illustrates an exemplary CT system 100 configured to allow fast and iterative image reconstruction. Particularly, the CT system 100 is configured to image a subject such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray radiation source 104 configured to project a beam of x-ray radiation 106 for use in imaging the patient. Specifically, the radiation source 104 is configured to project the x-rays 106 towards a detector array 108 positioned on the opposite side of the gantry 102. Although FIG. 1 depicts only a single radiation source 104, in certain embodiments, multiple radiation sources may be employed to project a plurality of x-rays 106 for acquiring projection data corresponding to the patient at different energy levels.

In certain embodiments, the CT system 100 further includes an image processing unit 110 configured to reconstruct images of a target volume of the patient using an iterative or analytic image reconstruction method. For example, the image processing unit 110 may use an analytic image reconstruction approach such as filtered backprojection (FBP) to reconstruct images of a target volume of the patient. As another example, the image processing unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the patient.

Figure 2:
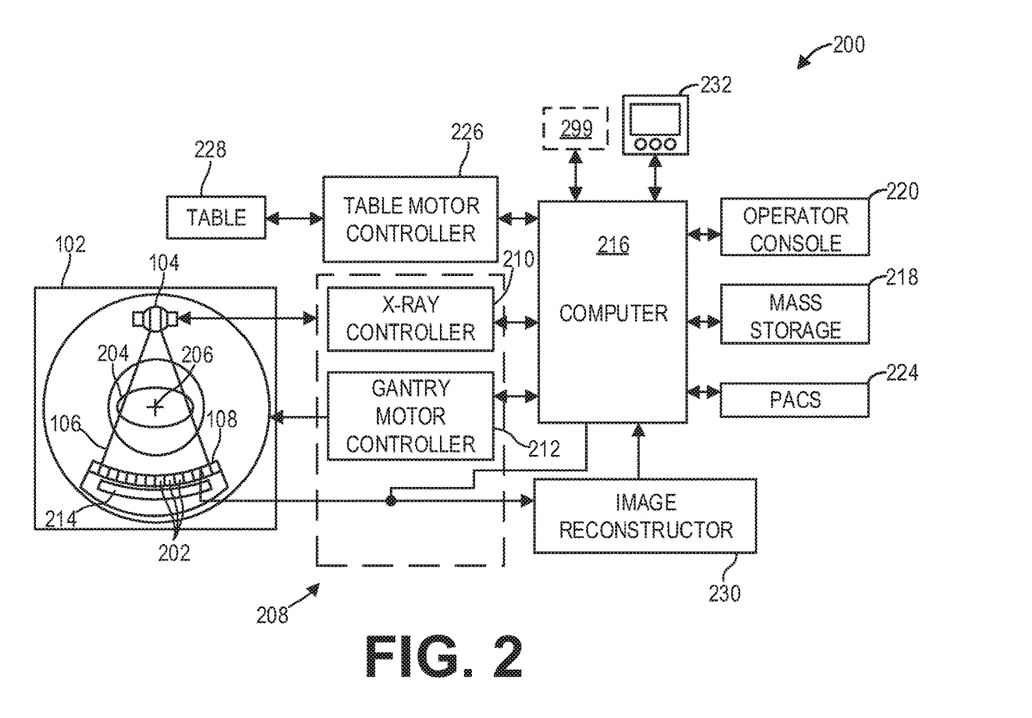
FIG. 2 shows a block schematic diagram of an exemplary imaging system according to an embodiment of the invention.

FIG. 2 illustrates an exemplary imaging system 200 similar to the CT system 100 of FIG. 1. In accordance with aspects of the present disclosure, the system 200 is configured to perform automatic exposure control. In one embodiment, the system 200 includes the detector array 108 (see FIG. 1). The detector array 108 further includes a plurality of detector elements 202 that together sense the x-ray beams 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

In one embodiment, the system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computing device (also referred to as processor) 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage device.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen, as non-limiting examples, to allow the operator to specify the commands and/or scanning parameters.

Although FIG. 2 illustrates only one operator console 220, more than one operator console may be coupled to the system 200, for example, for inputting or outputting system parameters, requesting examinations, and/or viewing images. Further, in certain embodiments, the system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the system 200 either includes, or is coupled to a picture archiving and communications system (PACS) 224. In an exemplary implementation, the PACS 224 is further coupled to a remote system such as a radiology department information system, hospital information system, and/or to an internal and/or external network (not shown) to allow operators at different locations to supply commands and parameters and/or gain access to the image data.

The computing device 216 uses the operator-supplied and/or system-defined commands and parameters to operate a table motor controller 226, which in turn, may control a motorized table 228. Particularly, the table motor controller 226 moves the table 228 for appropriately positioning the subject 204 in the gantry for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the system 200 and instead the computing device 216 may perform one or more functions of the image reconstructor 230. Moreover, the image reconstructor 230 may be located locally or remotely, and may be operatively connected to the system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Additionally or alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230. In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

In some embodiments, the system optionally includes an optical instrument 299 communicatively coupled to the computer 216. As discussed further herein, the computer 216 may be configured to measure, via the optical instrument 299, a size of the subject 204, and determine an attenuation profile of the subject 204 based on the measured size of the subject 204. To that end, optical instrument 299 may comprise one of a camera or a laser system coupled to the gantry 102. In examples wherein optical instrument 299 comprises a camera, the computer 216 may estimate the attenuation of the subject 204 based on images received from the camera 299. In examples wherein optical instrument 299 comprises a laser system, the computer 216 may estimate the attenuation of the subject based on laser measurements of the subject size received from the laser system 299.

Previous approaches to automatic exposure control for CT imaging systems exclusively use tube current modulation in order to control the noise properties in the image. The typical approach for automatic exposure control comprises manipulating the tube current based on the attenuation using a function such as:

$$I(d) = I(d_0)\left(\frac{A(d)}{A(d_0)}\right)^\alpha,$$

where I comprises the tube current, $d_0$ comprises a reference path length, A comprises the attenuation, and α comprises a modulation factor. FIG. 3 shows a graph 300 illustrating example attenuation-based tube current modulations for controlling image noise. In particular, graph 300 includes various plots illustrating how relative tube current is modulated as a function of relative attenuation for various values of the modulation factor α.

Plot 302 illustrates an unmodulated tube current or constant dose wherein the relative tube current is equal to 1 regardless of the relative attenuation. Plot 305 illustrates relative tube current as a function of relative attenuation for α equal to one, which provides constant image noise across a reconstruction volume.

Plot 310 illustrates relative tube current as a function of relative attenuation for α equal to 0.5, corresponding to a strong tube current modulation. Plot 312 illustrates relative tube current as a function of relative attenuation for α equal to 0.4, corresponding to a medium tube current modulation. Plot 314 illustrates relative tube current as a function of relative attenuation for modulation factor α equal to 0.3, corresponding to a weak tube current modulation.

As described further herein, another approach to automatic exposure control is helical pitch modulation, wherein the helical pitch is varied based on attenuation during a scan. In one illustrative and non-limiting example, the pitch may be varied based on attenuation according to:

$$P(d) = P(d_0)\left(\frac{A(d_0)}{A(d)}\right)^\alpha,$$

where P comprises the helical pitch. Note that the pitch is inversely proportional to the attenuation, whereas the tube current is proportional to the attenuation.

To illustrate, FIG. 4 shows a graph 400 illustrating example attenuation-based pitch modulations for controlling image noise. In particular, graph 400 includes various plots illustrating how relative helical pitch may be modulated as a function of relative attenuation for various values of the modulation factor $\alpha$.

Plot 402 illustrates an unmodulated pitch which provides a constant dose for all relative attenuations. Plot 405 illustrates relative pitch as a function of relative attenuation for a modulation factor $\alpha$ equal to one, which provides a constant image noise level across a reconstruction volume.

Plot 410 illustrates relative pitch as a function of relative attenuation for a modulation factor $\alpha$ equal to 0.5, which corresponds to a strong pitch modulation. Plot 412 illustrates relative pitch as a function of relative attenuation for a modulation factor $\alpha$ equal to 0.4, which corresponds to a medium pitch modulation. Plot 414 illustrates relative pitch as a function of relative attenuation for a modulation factor $\alpha$ equal to 0.3, which corresponds to a weak pitch modulation.

Figure 5:
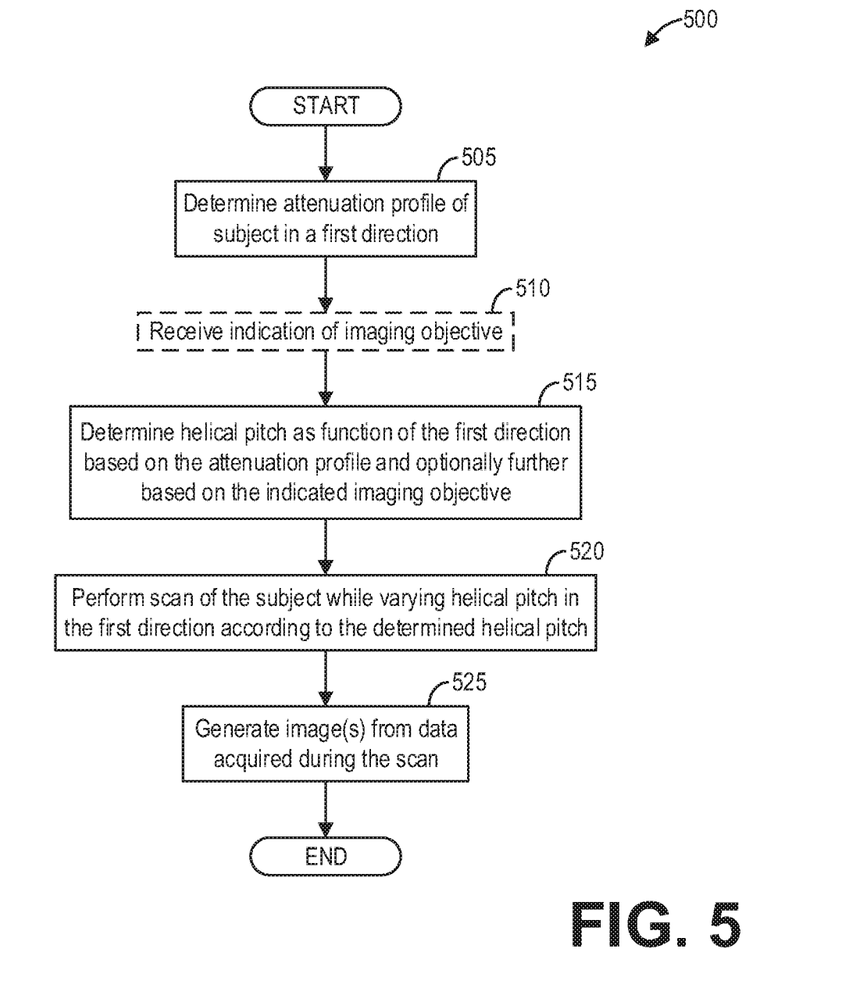
FIG. 5 shows a high-level flow chart illustrating an example method for automatic exposure control according to an embodiment of the invention.

FIG. 5 shows a high-level flow chart illustrating an example method 500 for automatic exposure control. Method 500 relates to performing a CT scan of a subject, such as a patient, while varying the helical pitch for automatic exposure control. Method 500 will be described herein with reference to the system depicted in FIGS. 1 and 2, though it should be understood that the method may be applied to other systems and components without departing from the scope of this disclosure. Method 500 may be carried out by computer 216, and may be stored as executable instructions in non-transitory memory of the computer 216.

Method 500 begins at 505. At 505, method 500 includes determining an attenuation profile of a subject in a first direction. The subject comprises a patient or other object being scanned, while the first direction comprises the direction along which the patient is moved during the scan, such as the z axis as depicted in FIG. 1 or, more generally, the axis or direction normal to the imaging plane of the imaging system.

In one example, an attenuation profile of a subject is obtained from one or more scout images. To that end, determining an attenuation profile comprises performing a scout scan of the subject to acquire scout data. The scout data comprises, as an example, two orthogonal views from each slice position in the prescribed scan, one at a gantry angle of 0° and the other at an angle of 90°. In a typical scout scan, the two orthogonal scout projections are acquired at a succession of slice locations along the z axis over the entire anatomy or region to be imaged. The acquired scout projections or scout data may then be processed (e.g., filtered, corrected, normalized, and so on). An attenuation profile is determined from the processed, or in some examples the unprocessed, scout projections. Additionally, a very low dose three-dimensional image may be used as scout or planning data.

In some examples, the attenuation profile is determined from two-dimensional scout images. In other examples, the attenuation profile is determined from three-dimensional scout images. In such examples, the scout scan may comprise a low-dose scan of the subject.

In another example, determining the attenuation profile of the subject comprises estimating a size of the subject based on a camera fixed to or otherwise positioned adjacent to the gantry of the imaging system.

In another example, the attenuation profile of the subject is obtained from a previous scan of the subject. For example, if a patient received a previous CT scan during another imaging session, one or more of the images obtained during the previous CT scan may be retrieved from non-transitory memory. The attenuation profile may then be determined based on the one or more CT images.

In yet another example, the attenuation profile may be determined via an optical system such as a laser system fixed to or otherwise positioned adjacent to the imaging system. For example, a laser system may be used to measure the size of the subject, and the attenuation profile may be estimated or otherwise calculated based on the measured size of the subject.

At 510, method 500 optionally includes receiving an indication of an imaging objective. As an illustrative example, an operator of the imaging system may select, via an operator console such as operator console 220, an imaging objective. As another example, method 500 automatically selects the imaging objective based on a training procedure and information gathered on different clinical tasks in each given anatomical region. The imaging objective may vary based on the given anatomy to be scanned and/or a clinical task.

In one example, the imaging objective comprises an image quality objective. For example, the image quality objective may comprise equal noise throughout the image volume. As another example, the image quality object may comprise equal noise in a region of interest (ROI).

At 515, method 500 includes determining helical pitch as a function of the first direction based on the attenuation profile and optionally further based on the indicated imaging objective. Determining helical pitch based on the attenuation profile may comprise applying a transfer function to the attenuation profile to obtain the desired pitch modulation as a function of the first direction (e.g., the z direction).

As an illustrative and non-limiting example, FIG. 6 shows a graph 600 illustrating an example attenuation profile 605 obtained from a scout projection image. In particular, attenuation profile 605 depicts the attenuation of a patient as a function of position along the z axis. As discussed above, the helical pitch modulation P(z) is inversely proportional to the attenuation profile A(z):

$$P(z) \propto A(z)^{-\alpha}.$$

Therefore, method 500 may calculate a helical pitch modulation by inverting the attenuation profile 605. FIG. 7 shows a graph 700 illustrating an example helical pitch modulation 705 obtained from the attenuation profile 605. In particular, helical pitch modulation 705 is obtained from the attenuation profile 605 by using a modulation factor $\alpha$ equal to one in order to achieve constant image noise as a function of z. In some examples, the modulation factor $\alpha$ may be automatically selected based on the indicated imaging objective (i.e., clinical task, anatomical region being scanned, desired image quality, and so on).

In some examples, the helical pitch modulation 705 may be modified so that the helical pitch modulation is physically realizable. That is, the table motion and gantry rotation are physically limited, and so the helical pitch modulation must be modified based on system constraints. For example, the helical pitch modulation may be smoothed to avoid erratic table accelerations and/or gantry rotation accelerations. Furthermore, the helical pitch modulation may be further constrained based on the imaging task and the anatomical location being scanned. In some examples, the helical pitch modulation may be further constrained based on the reconstruction algorithm. To that end, the reconstruction chain may, in some examples, limit the pitch even if the table can physically achieve a higher pitch. Given the constraints of the system and the reconstruction algorithms, the helical pitch modulation may be capped or limited to a given range. As an illustrative example, FIG. 8 shows a graph 800 illustrating an example modified pitch modulation 805. In particular, modified pitch modulation 805 comprises the helical pitch modulation 705 after smoothing and capping the helical pitch modulation 705. In the illustrated example, the modified pitch modulation 805 is constrained between a relative pitch of 0.5 and 1.4, and the irregularities of helical pitch modulation 705 are smoothed as seen in the region of modified pitch modulation 805 near the z position of 200.

Thus, referring again to FIG. 5, determining the helical pitch based on the attenuation profile and further on the indicated imaging objective may comprise applying a transfer function to the attenuation profile, smoothing the resulting helical pitch modulation, and capping the smoothed helical pitch modulation.

At 520, method 500 includes performing a scan of the subject while varying the helical pitch in the first direction according to the determined helical pitch. As discussed herein above, helical pitch comprises the linear distance along the axis of the helix (e.g., the z direction) traveled during one gantry rotation. Thus, varying the helical pitch may comprise adjusting the table velocity, adjusting the gantry rotation speed, or combinations thereof.

In one example, varying the helical pitch in the first direction comprises dynamically varying the table velocity in the z direction during the scan. The table velocity is dynamically varied while the gantry rotation speed is held constant during the scan according to the pitch modulation determined at 515.

In another example, varying the helical pitch in the first direction comprises dynamically varying the gantry rotation speed during the scan. In this example, the gantry rotation speed is dynamically varied while the table velocity is held constant during the scan according to the pitch modulation determined at 515.

In yet another example, varying the helical pitch in the first direction comprises dynamically varying the table velocity and the gantry rotation speed during the scan. In this example, both the table velocity and the gantry rotation are dynamically varied during the scan according to the pitch modulation determined at 515.

At 525, method 500 includes generating one or more images from data acquired during the scan. Generating images from the acquired scan data comprises using an image reconstruction algorithm to reconstruct an image from the acquired data. Further, the images may be generated or reconstructed based on the varied helical pitch used during the scan. In one example, the standard analytic image reconstruction is applied with fixed weights based on the dynamic pitch. In another example, the weights in the image reconstruction are calculated based on the dynamic acquisition. In yet another example, an iterative reconstruction algorithm is used to generate the images. In this way, the reconstruction of the one or more images may take into account the variable helical pitch, thereby avoiding or at least reducing the presence of image artifacts that would otherwise occur if the image reconstruction were performed with the assumption of a constant or non-dynamic helical pitch.

After generating the one or more images, the one or more images may be transmitted to a display for review by an operator of the imaging system, transmitted to a PACS such as PACS 224, stored in mass storage such as mass storage 218 for subsequent retrieval, and so on. Method 500 then ends.

Thus, the radiation dose may be reduced while maintaining a desired image quality and without modulating a tube current.

Furthermore, in some examples, the modulation of the helical pitch may be constrained by contrast injection timing. For example, if contrast is used during a scan, an upper limit to the relative helical pitch may be implemented to account for the contrast injection timing.

FIG. 9 shows a high-level flow chart illustrating an example method 900 for automatic exposure control. Specifically, method 900 relates to performing automatic exposure control by varying the helical pitch, varying the tube current, or varying both the helical pitch and the tube current. Method 900 will be described herein with reference to the system depicted in FIGS. 1 and 2, though it should be understood that the method may be applied to other systems and components without departing from the scope of this disclosure. Method 900 may be carried out by computer 216, and may be stored as executable instructions in non-transitory memory of the computer 216.

Method 900 begins at 905. At 905, method 900 includes performing a scout scan of a subject. The scout scan may comprise a low dose 2D or 3D CT scan. Continuing at 910, method 900 includes determining an attenuation profile based on the scout scan.

At 915, method 900 includes determining whether tube current ("mA") modulation will be used for automatic exposure control. The imaging system may only employ tube current modulation for automatic exposure control in certain imaging modes, and may not employ tube current modulation in other imaging modes, due to the design of the imaging system. For example, tube current modulation may not be employed during a dual energy spectral imaging mode, though it should be appreciated that in some examples, tube current modulation may be employed during dual energy imaging modes. Additionally or alternatively, an operator of the imaging system may manually select, for example via an operator console, whether or not tube current modulation is utilized during a scan.

If tube current modulation will not be used for automatic exposure control ("NO"), method 900 proceeds to 920. At 920, method 900 includes determining helical pitch modulation based on the attenuation profile. The helical pitch modulation may include a modulation of the table speed, the gantry rotation speed, or a combination thereof. At 925, method 900 includes performing a scan of the subject with the determined helical pitch.

However, referring again to 915, if tube current modulation will be used for automatic exposure control ("YES"), method 900 proceeds to 930. At 930, method 400 determines whether tube current modulation is sufficient. The tube current may be limited to a certain current range, and thus may be insufficient for automatic exposure control for some subjects with a large attenuation range, for example.

If tube current modulation is sufficient ("YES"), method 900 proceeds to 935. At 935, method 900 includes determining tube current modulation. Tube current modulation may be determined based on the attenuation profile, for example as described herein above with regard to FIG. 3. After determining the tube current modulation, method 900 continues to 937. At 937, method 900 includes performing a scan of the subject with the determined tube current modulation.

However, referring again to 930, if the tube current modulation is not sufficient ("NO"), method 900 proceeds to 940. At 940, method 900 includes determining a tube current modulation based on the attenuation profile. In some examples, the tube current may be modulated according to the angular position of the x-ray source in addition or alternative to the linear position of the x-ray source.

At 942, method 900 includes determining a helical pitch modulation based on the attenuation profile and the determined tube current modulation. For example, the tube current may be modulated within the operating range of the tube, and the helical pitch may be modulated to provide the desired automatic exposure control in combination with the tube current modulation. Continuing at 944, method 900 includes performing a scan of the subject with the determined helical pitch modulation and tube current modulation. That is, the subject is scanned while the tube current is modulated according to the tube current modulation determined at 940 while the helical pitch is modulated according to the helical pitch modulation determined at 942. In this way, the desired automatic exposure control can be realized based on a combination of tube current modulation and helical pitch modulation.

In some examples, the helical pitch modulation may be determined prior to determining the tube current modulation. For example, the tube current can be modulated more quickly than the helical pitch due to the physical constraints of helical pitch adjustments. Thus, the helical pitch modulation may comprise a coarse automatic exposure control while the tube current modulation may comprise a fine automatic exposure control.

After a scan is performed at either 925, 937, or 944, method 900 proceeds to 945. At 945, method 900 includes generating one or more images from data acquired during the scan. Generating the one or more images from the acquired scan data comprises using an image reconstruction algorithm to reconstruct an image from the acquired data. Further, the images may be generated or reconstructed based on the varied helical pitch and/or the varied tube current used during the scan. In one example, the standard analytic image reconstruction is applied with fixed weights based on the dynamic pitch and/or dynamic tube current. In another example, the weights in the image reconstruction are calculated based on the dynamic acquisition. In yet another example, an iterative reconstruction algorithm is used to generate the images. The iterative reconstruction algorithm may be modified based on the variable helical pitch and/or variable tube current. Note that when using iterative reconstruction, the relative pitch may be modulated differently than the pitch may be modified for analytic reconstruction. In this way, the reconstruction of the one or more images may take into account the variable helical pitch and/or variable tube current, thereby avoiding or at least reducing the presence of image artifacts that would otherwise occur if the image reconstruction were performed with the assumption of a constant or non-dynamic helical pitch and/or a constant or non-dynamic tube current.

Continuing at 950, method 900 includes displaying the one or more images, for example via a display device such as display device 232. The one or more images may additionally or alternatively be transmitted to a PACS such as PACS 224 and/or stored in mass storage such as mass storage 218 for subsequent retrieval. Method 900 then ends.

To illustrative the efficacy of helical pitch modulation in comparison to tube current modulation, FIG. 10 shows a graph 1000 illustrating example image noise for different approaches to automatic exposure control. Specifically, graph 1000 illustrates the relative noise measured for different slice locations in z for two standard pitch modes, a variable pitch acquisition, and a tube current modulation with fixed helical pitch. The relative noise is the noise in a given slice divided by the average over all slices.

Specifically, plot 1002 illustrates the normalized noise standard deviation across measured image slices in a reconstruction volume, wherein the image slices are reconstructed from data acquired during a scan which utilized the variable helical pitch techniques described herein. Plot 1004 illustrates the normalized noise standard deviation across measured image slices in a reconstruction volume, wherein the image slices are reconstructed from data acquired during a scan which utilized tube current modulation. As depicted in the graph 1000, the helical pitch modulation has a slightly better noise performance (i.e., a lower noise standard deviation) compared to the tube current modulation from measured slice 0 through measured slice 5, while the tube current modulation has a slightly better noise performance compared to the helical pitch modulation from measured slice 5 to measured slice 10. It should be appreciated that the dynamic range in noise is comparable between the variable pitch and the tube current modulation.

Meanwhile, plots 1012 and 1014 correspond to acquisitions with a fixed (relative) helical pitch of 0.5 and 1.375, respectively, and without tube current modulation. For the standard helical pitch acquisitions illustrated by 1012 and 1014, the noise varies by more than the average standard deviation, and this is significantly reduced for variable helical pitch and tube current modulation illustrated respectively by plots 1002 and 1004.

Although the methods described herein above include determining attenuation of a subject prior to performing a helical scan, it should be appreciated that in some examples, the attenuation of the subject may be evaluated and the helical pitch adjusted responsive thereto in real-time during the scan. In other words, in some examples, the methods may not rely on predetermining an attenuation profile prior to the helical scan.

As an illustrative and non-limiting example, FIG. 11 shows a high-level flow chart illustrating an example method 1100 for automatic exposure control with dynamic helical pitch according to an embodiment. Specifically, method 1100 relates to estimating attenuation of a subject in real-time during a scan and varying the helical pitch based on the estimated attenuation. Method 1100 will be described herein with reference to the system depicted in FIGS. 1 and 2, though it should be understood that the method may be applied to other systems and components without departing from the scope of this disclosure. Method 1100 may be carried out by computer 216, and may be stored as executable instructions in non-transitory memory of the computer 216.

Method 1100 may optionally begin at 1102. At 1102, method 100 may optionally include performing a scout scan of a subject, such as a patient or an object. The scout scan may comprise a low dose 2D or 3D CT scan.

Method 1100 continues at 1105. At 1105, method 1100 may optionally include receiving an indication of an imaging objective. As an illustrative example, an operator of the imaging system may select, via an operator console such as operator console 220, an imaging objective. As another example, method 500 automatically selects the imaging objective based on a training procedure and information gathered on different clinical tasks in each given anatomical region. The imaging objective may vary based on the given anatomy to be scanned and/or a clinical task. In one example, the imaging objective comprises an image quality objective. For example, the image quality objective may comprise equal noise throughout the image volume. As another example, the image quality object may comprise equal noise in a region of interest (ROI).

In examples wherein method 1100 does not include receiving an indication of an imaging objective at 1105, for example if the operator does not select an imaging objective, the imaging system may include a default imaging objective. For example, the default imaging objective may comprise equal noise through the image volume as described hereinabove.

At 1110, method 1100 includes beginning a helical scan of a subject, such as a patient or an object. After beginning the helical scan, at 1115, method 1100 includes estimating attenuation of the subject. In one example, estimating attenuation of the subject comprises, while the system is scanning the subject at a particular z location of the subject, reconstructing image slice(s) at the z location as the projection data is acquired and estimating the attenuation at the z location based on the reconstructed image slice(s).

Additionally or alternatively, the method may predict the attenuation of the subject at a subsequent z position of the subject based on the estimated attenuation, for example using statistical methods that may take into account factors such as the general size of the subject (e.g., patient weight and height), and attenuation profiles of other subjects with similar and/or dissimilar sizes. For example, the method may utilize a machine learning algorithm trained on a plurality of attenuation profiles of patients to predict, in real-time, the attenuation of a patient at a next z location to be scanned based on estimated attenuation at a current z location as well as the prior training of the algorithm. As more subjects are scanned, the prediction accuracy may increase due to the larger number of training samples.

In another example, the imaging system may include a camera or other optical system configured to determine the size of the subject at the location being scanned. The attenuation of the subject may thus be estimated based on information received therefrom.

In examples wherein method 1100 includes performing a scout scan at 1102, the method may initially estimate the attenuation of the subject based on the scout scan as described hereinabove. The initial estimate based on the scout scan may then be updated and improved based on the real-time attenuation estimates described hereinabove.

After estimating the attenuation of the subject, method 1100 continues to 1120. At 1120, method 1100 includes adjusting the helical pitch based on the estimated attenuation. Adjusting the helical pitch may comprise adjusting the table speed, adjusting the gantry rotation speed, or a combination thereof.

Adjustments to the helical pitch may be constrained based on the physical limitations of the imaging system components. For example, if the estimated attenuation at a particular z location is substantially different from the estimated attenuation at an immediately preceding z location, such that the corresponding change in helical pitch would be substantial, the helical pitch may be adjusted by a smaller amount in order to avoid irregular or erratic shifts in helical pitch. In other words, adjustments to the helical pitch may be smoothed in real-time.

At 1122, method 1100 includes determining whether the scan is complete. If the scan is not complete ("NO"), method 1100 continues scanning at 1123. Method 1100 further returns to estimating the attenuation of the subject at 1115 and adjusting the helical pitch based on the estimated attenuation at 1120 until the scan is complete ("YES"). In this way, the attenuation of the subject may be continuously estimated and the helical pitch dynamically adjusted responsive thereto during a scan.

When the scan is completed ("YES"), method 1100 proceeds from 1122 to 1125. At 1125, method 1100 ends the helical scan. At 1130, method 1100 includes generating one or more images from data acquired during the helical scan. Generating images from the acquired scan data comprises using an image reconstruction algorithm to reconstruct an image from the acquired data.

Further, the images may be generated or reconstructed based on the varied helical pitch used during the scan. In one example, the standard analytic image reconstruction is applied with fixed weights based on the dynamic pitch. In another example, the weights in the image reconstruction are calculated based on the dynamic acquisition. In yet another example, an iterative reconstruction algorithm is used to generate the images. In this way, the reconstruction of the one or more images may take into account the variable helical pitch, thereby avoiding or at least reducing the presence of image artifacts that would otherwise occur if the image reconstruction were performed with the assumption of a constant or non-dynamic helical pitch.

After generating the one or more images, the one or more images may be transmitted to a display for review by an operator of the imaging system, transmitted to a PACS such as PACS 224, stored in mass storage such as mass storage 218 for subsequent retrieval, and so on. Method 1100 then ends.

A technical effect of the disclosure is the modulation of a helical pitch during a helical scan of a subject. Another technical effect of the disclosure is a reduced dose received by a subject being scanned. Another technical effect of the disclosure is the reconstruction of an image from projection data acquired during a scan wherein the helical pitch is dynamically varied. Yet another technical effect is the modulation of a table speed during a helical acquisition. Another technical effect is the modulation of a gantry rotational speed during a helical acquisition.

In one embodiment, a method comprises estimating attenuation properties of a subject along a direction, and varying, based on the attenuation properties, a helical pitch along the direction during a scan of the subject.

In a first example of the method, the attenuation properties are estimated based on one or more scout images of the subject. In a second example of the method optionally including the first example, the attenuation properties are estimated based on measurements acquired via an optical instrument positioned on the imaging system. The optical instrument may comprise a camera or a laser system. In a third example of the method optionally including one or more of the first and second examples, varying the helical pitch is further based on a desired imaging objective. In a fourth example of the method optionally including one or more of the first through third examples, the desired imaging objective is based on one or more of a clinical task and an anatomy to be imaged. In a fifth example of the method optionally including one or more of the first through fourth examples, the desired imaging objective comprises a desired image noise level throughout at least a portion of an image reconstructed from data acquired during the scan. In a sixth example of the method optionally including one or more of the first through fifth examples, the method further comprises automatically selecting the desired imaging objective based on a training procedure and information gathered on different clinical tasks in each given anatomical region. In a seventh example of the method optionally including one or more of the first through sixth examples, the method further comprises varying a tube current based on the attenuation properties to meet the desired imaging objective. In an eighth example of the method optionally including one or more of the first through seventh examples, varying the helical pitch comprises varying a table velocity during the scan, varying a gantry rotation velocity during the scan, or a combination thereof. In a ninth example of the method optionally including one or more of the first through eighth examples, the method further comprises reconstructing one or more images from data acquired during the scan. In a tenth example of the method optionally including one or more of the first through ninth examples, the reconstruction of the one or more images is adjusted based on the varied helical pitch. In an eleventh example of the method optionally including one or more of the first through tenth examples, the attenuation properties are estimated during the scan.

In another embodiment, a method comprises: determining an attenuation profile of a subject in a first direction; determining a modulation of a helical pitch in the first direction based on the attenuation profile; performing a helical scan of the subject while varying the helical pitch in the first direction according to the modulation; and generating an image from data acquired during the scan.

In a first example of the method, the attenuation profile is determined from one of a two-dimensional scout image of the subject, a three-dimensional scout image of the subject, a prior diagnostic image of the subject, measurements of the subject acquired by a camera, and measurements of the subject acquired by a laser system. In a second example of the method optionally including the first example, determining the modulation of the helical pitch based on the attenuation profile comprises generating a modulation profile by applying a transfer function to the attenuation profile, and generating the modulation by smoothing and capping the modulation profile. In a third example of the method optionally including one or more of the first and second examples, varying the helical pitch according to the modulation comprises varying a table speed of a table upon which the subject is positioned according to the modulation, varying a rotational speed of a gantry rotating about the subject during the scan according to the modulation, or varying the table speed and the rotational speed according to the modulation.

In yet another embodiment, a system comprises: a gantry, the gantry defining a bore; an x-ray source that emits a beam of x-rays toward an object to be imaged, the x-ray source positioned on the gantry; a detector that receives the x-rays attenuated by the object, the detector positioned on the gantry; a table upon which the object is positioned, the table configured to move the object through the bore; a data acquisition system (DAS) operably connected to the detector; and a computer operably connected to the DAS and configured with instructions in non-transitory memory that when executed cause the computer to: estimate attenuation properties of the object along a direction; and vary, based on the attenuation properties, a helical pitch along the direction during a scan of the subject.

In a first example of the system, the computer is further configured with instructions in the non-transitory memory that when executed cause the computer to adjust a rotational speed of the gantry to vary the helical pitch. In a second example of the system optionally including the first example, the computer is further configured with instructions in the non-transitory memory that when executed cause the computer to adjust a speed of the table through the bore to vary the helical pitch. In a third example of the system optionally including one or more of the first and second examples, the system further comprises a display device communicatively coupled to the computer, and the computer is further configured with instructions in the non-transitory memory that when executed cause the computer to reconstruct at least one image from data acquired during the scan, and display, via the display device, the at least one image, wherein the reconstruction is adjusted based on the varied helical pitch.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   estimating attenuation properties of a subject along a direction prior to a computed tomography scan of the subject; and
   varying, based on the attenuation properties, a helical pitch along the direction during the computed tomography scan of the subject, wherein varying the helical pitch along the direction during the computed tomography scan comprises increasing and decreasing the helical pitch at positions along the direction of decreased attenuation and increased attenuation, respectively, indicated in the estimated attenuation properties along the direction.

2. The method of claim 1, wherein the attenuation properties are estimated based on one or more scout images of the subject, the one or more scout images of the subject acquired during a scout scan of the subject performed prior to the computed tomography scan.

3. The method of claim 1, wherein the attenuation properties are estimated based on measurements acquired via an optical instrument positioned on an imaging system, the optical instrument comprising one of a camera or a laser system.

4. The method of claim 1, wherein varying the helical pitch is further based on a desired imaging objective.

5. The method of claim 4, wherein the desired imaging objective is based on one or more of a clinical task and an anatomy to be imaged.

6. The method of claim 4, wherein the desired imaging objective comprises a desired image noise level throughout at least a portion of an image reconstructed from data acquired during the computed tomography scan.

7. The method of claim 4, further comprising automatically selecting the desired imaging objective based on a training procedure and information gathered on different clinical tasks in each given anatomical region.

8. The method of claim 4, further comprising varying a tube current based on the attenuation properties to meet the desired imaging objective.

9. The method of claim 1, wherein varying the helical pitch comprises dynamically varying a table velocity during the computed tomography scan, dynamically varying a gantry rotation velocity during the computed tomography scan, or a combination thereof.

10. The method of claim 1, further comprising reconstructing one or more images from data acquired during the computed tomography scan.

11. The method of claim 10, wherein the reconstruction of the one or more images is adjusted based on the varied helical pitch.

12. A method, comprising:
determining an attenuation profile of a subject in a first direction;
determining a modulation of a helical pitch in the first direction based on the attenuation profile;
performing a helical computed tomography scan of the subject while varying the helical pitch in the first direction according to the modulation; and
generating an image from data acquired during the helical computed tomography scan.

13. The method of claim 12, wherein the attenuation profile is determined from one of a two-dimensional scout image of the subject, a three-dimensional scout image of the subject, a prior diagnostic image of the subject, measurements of the subject acquired by a camera, and measurements of the subject acquired by a laser system.

14. The method of claim 12, wherein determining the modulation of the helical pitch based on the attenuation profile comprises generating a modulation profile by applying a transfer function to the attenuation profile, and generating the modulation by smoothing and capping the modulation profile.

15. The method of claim 12, wherein varying the helical pitch according to the modulation comprises varying a table speed of a table upon which the subject is positioned according to the modulation, varying a rotational speed of a gantry rotating about the subject during the helical computed tomography scan according to the modulation, or varying the table speed and the rotational speed according to the modulation.

16. A system, comprising:
a gantry, the gantry defining a bore;
an x-ray source that emits a beam of x-rays toward an object to be imaged, the x-ray source positioned on the gantry;
a detector that receives the x-rays attenuated by the object, the detector positioned on the gantry;
a table upon which the object is positioned, the table configured to move the object through the bore;
a data acquisition system (DAS) operably connected to the detector; and
a computer operably connected to the DAS and configured with instructions in non-transitory memory that when executed cause the computer to:
estimate attenuation properties of the object along a direction prior to a scan of the object; and
vary, based on the attenuation properties, a helical pitch along the direction during the scan of the object, wherein varying the helical pitch along the direction comprises increasing and decreasing the helical pitch at positions of decreased attenuation and increased attenuation, respectively, indicated in the attenuation properties.

17. The system of claim 16, wherein the computer is further configured with instructions in the non-transitory memory that when executed cause the computer to adjust a rotational speed of the gantry to vary the helical pitch.

18. The system of claim 16, wherein the computer is further configured with instructions in the non-transitory memory that when executed cause the computer to adjust a speed of the table through the bore to vary the helical pitch.

19. The system of claim 16, further comprising a display device communicatively coupled to the computer, wherein the computer is further configured with instructions in the non-transitory memory that when executed cause the computer to reconstruct at least one image from data acquired during the scan, and display, via the display device, the at least one image, wherein the reconstruction is adjusted based on the varied helical pitch.

20. The method of claim 12, wherein tube current is not modulated during the helical computed tomography scan.

* * * * *